(12) United States Patent
 Lakshminarayanan et al.

(10) Patent No.: US 11,179,255 B2
(45) Date of Patent: Nov. 23, 2021

(54) MEDICAL DEVICES

(71) Applicant: SAHAJANAND MEDICAL TECHNOLOGIES LIMITED, Surat (IN)

(72) Inventors: Ramanan Lakshminarayanan, Bangalore (IN); Dhirajlal Vallabhbhai Kotadia, Surat (IN); Bhautik Chandulal Khanpara, Surat (IN); Abhijeet Singhvi, Valsad (IN); Parth Pramodkumar Naik, Surat (IN)

(73) Assignee: SAHAJANAND MEDICAL TECHNOLOGIES LIMITED, Surat (IN)

( * ) Notice: Subject to any disclaimer, the term of this patent is extended or adjusted under 35 U.S.C. 154(b) by 0 days.

(21) Appl. No.: 16/636,711

(22) PCT Filed: Mar. 4, 2019

(86) PCT No.: PCT/IB2019/051717
§ 371 (c)(1),
(2) Date: Feb. 5, 2020

(87) PCT Pub. No.: WO2019/186296
PCT Pub. Date: Oct. 3, 2019

(65) Prior Publication Data
US 2020/0237537 A1    Jul. 30, 2020

(30) Foreign Application Priority Data
Mar. 29, 2018  (IN) .............................. 201821011999

(51) Int. Cl.
*A61F 2/915*    (2013.01)
*A61F 2/89*    (2013.01)

(52) U.S. Cl.
CPC ................ *A61F 2/915* (2013.01); *A61F 2/89* (2013.01); A61F 2002/91541 (2013.01); A61F 2002/91575 (2013.01); A61F 2250/0098 (2013.01)

(58) Field of Classification Search
CPC .... A61F 2/915; A61F 2/86; A61F 2/89; A61F 2002/91575; A61F 2002/91566; A61F 2002/91541; A61F 2250/0098
See application file for complete search history.

(56) References Cited

U.S. PATENT DOCUMENTS 6,939,376 B2    9/2005  Shulze et al.
7,846,361 B2    12/2010  Thatcher et al.
(Continued)

FOREIGN PATENT DOCUMENTS

WO    00/30563    6/2000

OTHER PUBLICATIONS

International Search Report for PCT/IB2019/051717 dated Jun. 14, 2019, 5 pages.
(Continued)

*Primary Examiner* — Dinah Baria
(74) *Attorney, Agent, or Firm* — Nixon & Vanderhye P.C.

(57) ABSTRACT

A medical device includes a tubular support structure having a plurality of ringlets arranged sequentially along a common longitudinal axis thereof, a plurality of long connecting elements and optionally, a plurality of short connecting elements to connect the plurality of ringlets. Each of the plurality of ringlet is formed by of plurality of crowns connected along a circumferential direction, each crown being formed by two straight struts arranged in V-shaped configuration. At least one of the plurality of long connecting elements connects adjacent ringlets. In addition, consecutive long connecting elements connecting adjacent ring-
(Continued)

lets are to form a mirror-reflection of each other about a radial plane of reflection.

21 Claims, 9 Drawing Sheets

(56) References Cited

U.S. PATENT DOCUMENTS

| | | |
|---|---|---|
| 8,545,550 B2 | 10/2013 | Shulze et al. |
| 9,375,810 B2 | 6/2016 | Mangiardi |
| 9,498,357 B2 | 11/2016 | Fischer |
| 9,629,940 B2 | 4/2017 | Thatcher et al. |
| 9,662,416 B2 | 5/2017 | Thatcher et al. |
| 9,737,646 B2 | 8/2017 | Jones-Mcmeans et al. |
| 9,750,624 B2 | 9/2017 | Mangiardi |
| 9,814,553 B1 | 11/2017 | Kleiner et al. |
| 9,907,640 B2 | 3/2018 | Seddon et al. |
| 10,195,062 B2 | 2/2019 | Mangiardi |
| 2003/0149469 A1 | 8/2003 | Wolinsky et al. |
| 2004/0236409 A1 | 11/2004 | Pelton et al. |
| 2014/0114434 A1 | 4/2014 | Cottone et al. |
| 2015/0112422 A1 | 4/2015 | Pazienza et al. |
| 2018/0116798 A1* | 5/2018 | Perszyk ................. A61F 2/848 |

OTHER PUBLICATIONS

Written Opinion of the ISA for PCT/IB2019/051717 dated Jun. 14, 2019, 7 pages.

* cited by examiner

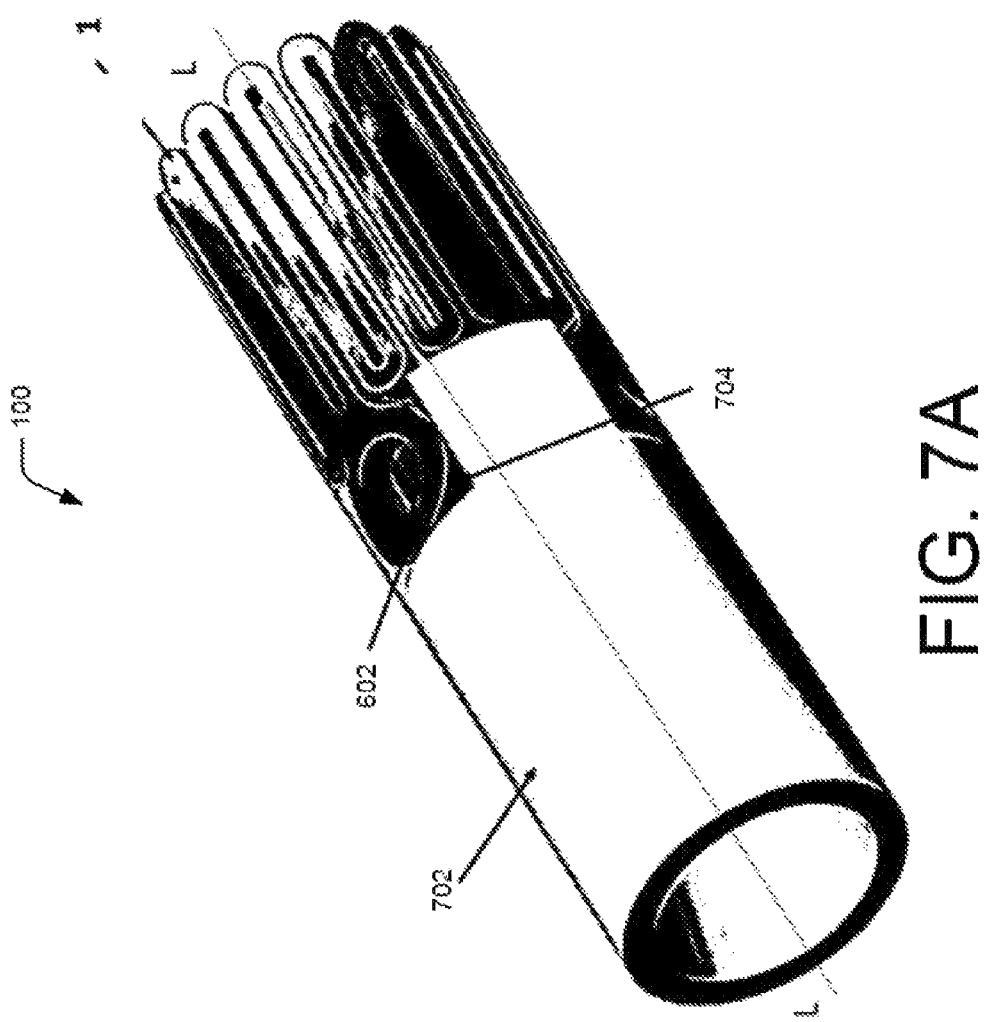

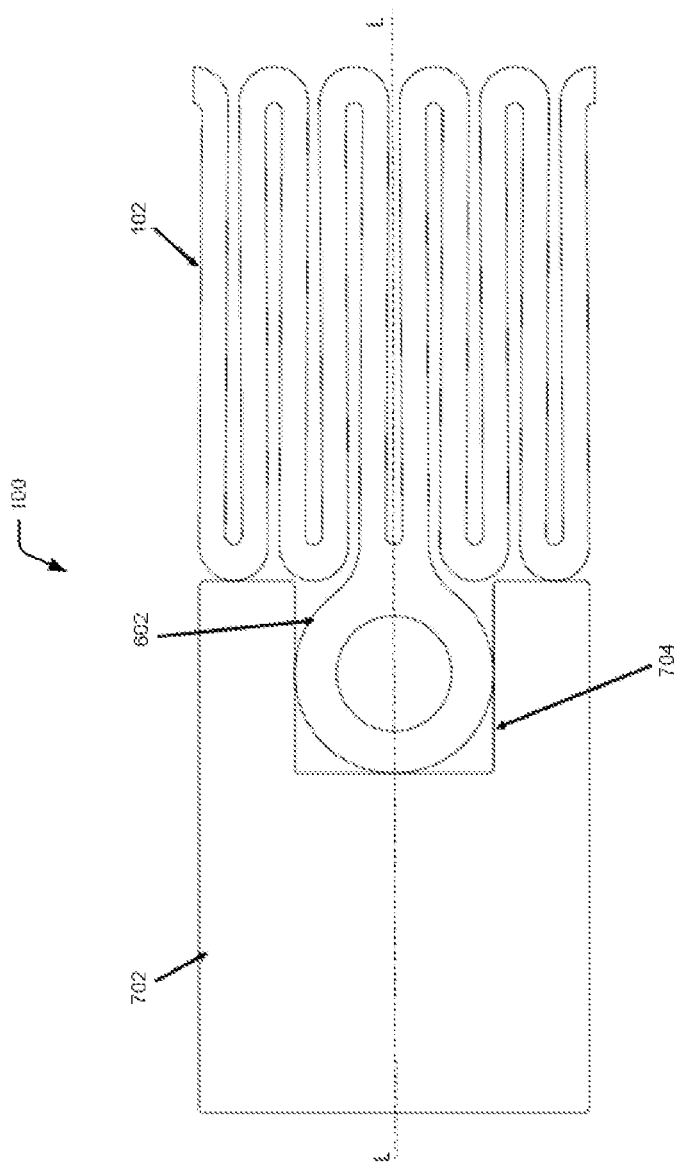

MEDICAL DEVICES

This application is the U.S. national phase of International Application No PCT/IB2019/051717, filed Mar. 4, 2019 which designated the U.S. and claims priority to Indian Application No. 201821011999, filed Mar. 29, 2018, the entire contents of each of which are hereby incorporated by reference.

TECHNICAL FIELD

The present subject matter relates, generally, to medical devices and, particularly but not exclusively, to medical devices for deployment in a lumen.

BACKGROUND

A stent is a tubular support frame made of a biocompatible metal, biostable polymer, biodegradable material, non-metals, bio-resorbable material or shape-memory alloys. The stent may be used in the lumen of humans as well as non-human animals, such as primates, horses, cows, pigs and sheep. Physiologically, the stent may be placed inside the lumen of any space, such as an artery, vein, bile duct, urinary tract, alimentary tract, tracheobronchial tree, cerebral aqueduct or genitourinary system, and may be balloon-expandable or self-expandable for being deployed in the lumen. For example, the stent may be deployed in blood vessels or organs, to prevent the lumen from collapsing. Therefore, in an example, the stent may be used in arteries, such as coronary, superficial femoral, and iliac, at a narrowed site to expand the vessel and to circumferentially support the vessel wall, to remedy blockages and/or narrowing of arteries that may otherwise cause obstruction of blood flow.

The stents are deployed at a target site using catheter-based procedures or similar interventional procedures into the intravascular region. The stent arrives at the target site in an initial crimped state and expands or is expanded, as the case may be, to a final state for deployment. In the process, the stent securely fixes inside the lumen against a wall of the lumen and provides the radial support to the lumen. For example, in case of a blood vessel, the stent expands the vessel from a clogged condition, thereby facilitating the recovery of blood flow in the clogged blood vessel and preventing elastic recoil and collapsing of the blood vessel. In said example, in addition, the stent also prevents local dissection of the blood vessel along a medial layer.

BRIEF DESCRIPTION OF DRAWINGS

The detailed description is provided with reference to the accompanying figures. It should be noted that the description and the figures are merely examples of the present subject matter, and are not meant to represent the subject matter itself.

FIGS. 7A and 7B illustrates a perspective view of a section of the medical device showing the tubular support structure attached with an end-stopper, according to yet another embodiment of the present subject matter.

Figure 1:
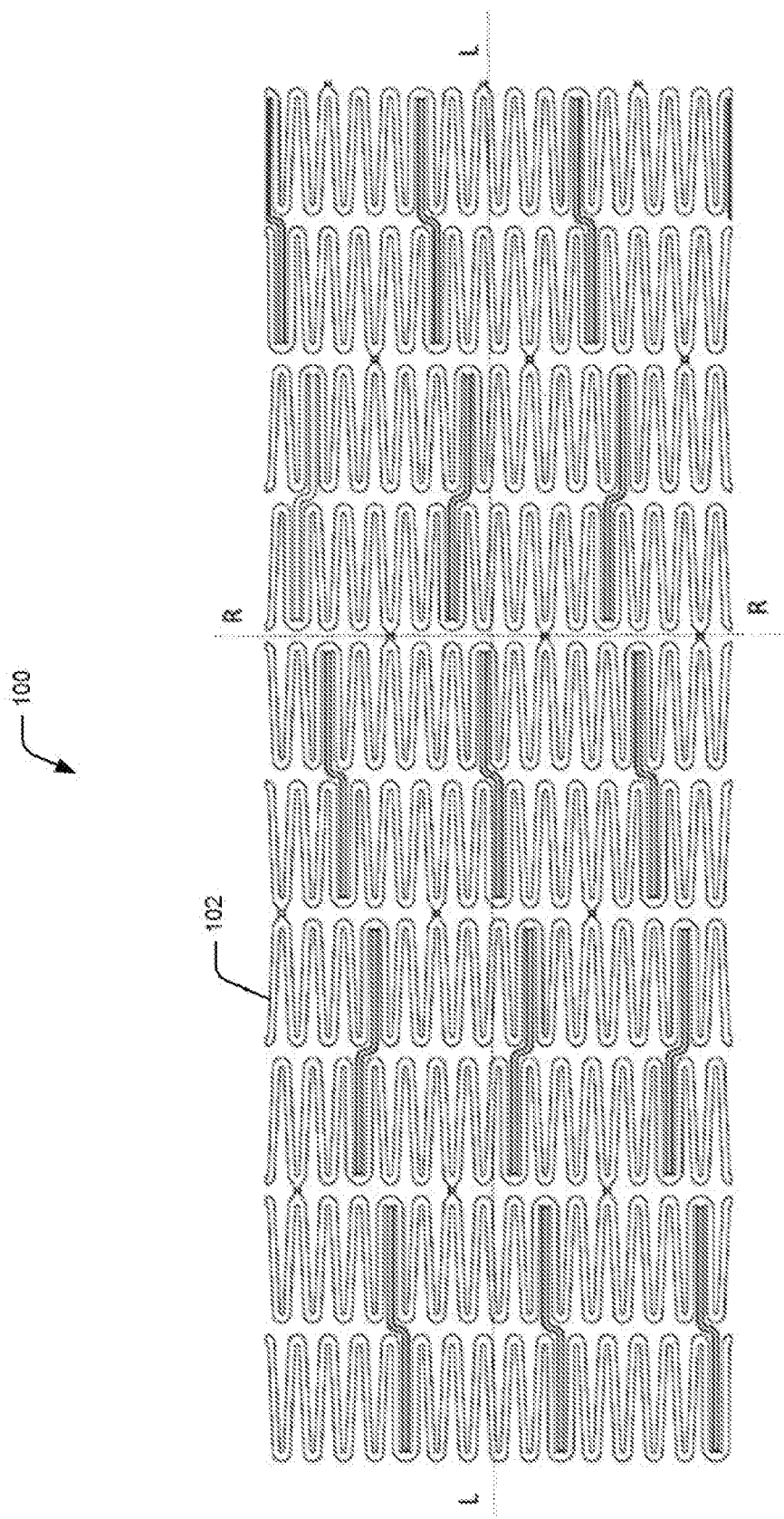
FIG. 1 illustrates a detailed view of a section of a medical device in a crimped state, according to an embodiment of the present subject matter.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

Generally, stents are designed in order to have certain inherent properties for effective operation. For example, the stents should be highly flexible to navigate through tortuous route inside the lumen and it should have sufficient stiffness and rigidity in the crimped state to be easily pushed through calcified lesions in the lumen. In addition, the stent should be able to take the shape and conform to the shape of the artery during deployment, and at the same time, should have sufficient radial strength and rigidity to provide adequate radial support to the artery to avoid prolapse after deployment. The stent should have a good expansion ratio with low recoil. Further, the design of the stent should be such that it allows the stent to be crimped without compromising with the design of the stent, for instance, allowing the stent to retain its original axial length after deployment.

In addition, stents are designed such that the design either restricts or accommodates the stress generated in the stent due to different mechanical forces applied on it at the time of deploying the stent or after the deployment. Most commonly, these mechanical forces are elongation, compression, torsional movement, bending movement and other physiological conditions e.g. blood flow (after the deployment). The combined effect of these forces, beyond a safe value, leads to fracturing of the joints in deployed stent and the fractured joints can give rise to many clinical complications e.g. recoiling, overlapping of adjacent ringlets and restenosis. Hence, fracture resistance is a major safety aspect of stent designing which can be enhanced by having design features that restrict or manage stress generation or stress concentration at potential locations to the minimum level by virtue of their design.

In order to meet the abovementioned criteria, the stents have different constructions, designs and properties each of which attempt to address different properties or a combination of the properties as mentioned above. However, due to design compromises, most of the stents meet only limited no. of properties and objectives outlined above, resulting in restricted utility and effectiveness.

For example, the tubular support frame of the stent may have many ringlet segments. The ringlet segments are formed by segment struts which are of a specific design and are sequentially arranged and joined in an endless manner to form a ring along the tubular shape of the stent. Further, these ringlet segments are joined longitudinally through connectors or connecting ties. The design of these connectors and their positioning between two adjoining ringlet segments substantially affects the design and performance of the stent either during the deploying of stent or post-deployment of the stent or both.

In another case, a stent can have a wave-like ringlet design without using straight struts. Further, in the present case, the stent is designed such that the ringlet segment or segment struts are wide at a mid-section. In addition, the stent may also include connecting tie-bars which are also formed as wave-like structure and connect peak-to-peak or valley-to-valley of the ringlets, at an offset. As a result, while the stent is highly flexible and has good stress distribution, the design compromises on longitudinal stiffness of the stent.

In another design, the stent utilizes long connectors to enhance flexibility, increased scaffolding and ability to absorb torsional forces. The stent includes angled (plate-shaped) struts and straight or angled connectors connecting the ringlet segments peak-to-peak at an offset. This structure can provide increased scaffolding, but increased stiffness in circumferential direction and overall stress in the stent during crimping.

In yet another design, the stent is a helical stent with bio-resorbable connectors. The connectors connect the crowns/ringlets in peak-to-peak fashion and can be of various shapes, such as curved, wave-like, or straight. The connectors connect the ringlets peak-to-peak at an angle or curved at 90° on both ends. In addition, the stent also includes straight connectors which connect valley-to-peak in the adjacent ringlets. This design, though, provides varying degree of flexibility to the stent, the stent lacks longitudinal stiffness. In addition, the flexibility of the connecting members may change after implantation. In addition, the straight connectors are to be released out of plane during bending, say due to bending of the balloon catheter used for deployment, and may pose a risk of damage to the lumen.

The present subject matter describes a medical device, such as a stent, that is designed to have a high degree of flexibility, significant radial strength, fracture resistance, and negligible axial length loss after deployment. The medical device, in accordance with the present subject matter, can have optimum levels of scaffolding, flexibility, and radial strength. At the same time, torsional forces in the medical device are balanced which is helpful in trackability and makes the medical device safe.

According to one aspect of the present subject matter, the medical device includes a tubular support structure comprising which is formed of a plurality of ringlets which are arranged sequentially along a common longitudinal axis thereof. In simpler language, the ringlets have coaxial central longitudinal axes. Each ringlet is formed by of plurality of crowns connected along a circumferential direction and, in turn, each crown is formed by two straight struts arranged in V-shaped configuration. The medical device further includes a plurality of long connecting elements, and at least one long connecting element connects adjacent ringlets. The long connecting element is Z-shaped and consecutive long connecting elements which connect adjacent ringlets form a mirror-reflection of each other about a radial plane of reflection. The radial plane of reflection can be a plane perpendicular to the common longitudinal axis of the ringlets of the medical device. Such a design provides a set of mechanical properties which allow easy insertion and manoeuvring of the medical device into lumens of small diameter having tortuous anatomy.

According to an aspect of the present subject matter, the long connecting element is of Z-shaped configuration and connects the valleys of adjacent ringlets, i.e. one end of the long connecting element is connected to a valley-type formation formed in one ringlet and the other end of the long connecting element is connected to a similar valley-type formation in the adjacent ringlet. The valley type configuration can be formed between two struts connected in V-shape in the crown. In an example, two adjacent ringlets are connected through long connecting elements at an offset between them.

The long connecting element can be formed of two long sections and a short section. In an example, the length of the short section can be equal to or greater than the shorter circumferential distance between one valley in one ringlet and the other valley in the adjacent ringlet connected by the long connecting element, as explained above. In addition, the short section connects the ends of the two long sections is such a way to form an obtuse angle between the short section and the long section, thereby forming the Z-shape of the long connecting element. As a design element of the medical device, the angle between the short section and the long section of the long connecting member is decided at the time of fabrication and remains fixed while crimping or expanding the tubular support structure. In an example, the angle can be between 91° and 160°, and the angles between one long section and the short section and the other long section and the short section can be substantially same.

As a result of such configuration of the long connecting element and the unchanging nature of the angle of the long connecting element, the length of the tubular support structure does not change axially after the tubular support structure is released to the normal state from the crimped state, for instance, in self-expansion operation. This feature of retaining original axial length of the tubular support structure after the deployment of the medical device provides enhanced accuracy in treatment of the lumen.

Further, in case the medical device is deployed by balloon expansion mechanism, the design of the long connecting element, in accordance with the present subject matter restricts or delays the axial contraction of the tubular support structure. Accordingly, the axial length of the tubular support structure may change in such a case, but the change is negligible. For instance, the axial length of the tubular support structure may change less than 5% of its original length after the deployment (after expansion), while being deployed using the balloon-expansion mechanism. In addition, at the time of fabrication, different expansion and flexural properties can be obtained by designing the angle between the short and long sections of the long connecting element.

Therefore, a properly selected and designed angle in the long connecting element improves safety and performance of the medical device. Angle present in the long connecting element provides improved trackability while the tubular support structure is being maneuvered through the lumen to reach the target site and also provides stability and radial stiffness too. Additionally, the angle present in the long connecting element provides flexibility to the tubular support structure and helps in addressing the variations in length due to crimping or expansion.

As mentioned previously, two consecutive Z-shaped long connecting elements are opposite or mirror-reflection to each other about a radial plane of reflection. In other words, the direction of the Z-shape of any two consecutive long connecting element, i.e., between any two consecutive ringlets is a mirror-reflection about the plane passing perpendicular to the longitudinal axis of the tubular support structure of the medical device. Such a design of the medical device provides stability, safety, trackability, fracture resistance, flexibility in crimped state, and also facilitates for negligible or no variation in the length of medical device structure either in crimped or expanded state.

Optionally, the medical device can further include a plurality of short connecting elements to supplement the long connecting elements in connecting the ringlets in the medical device. The short connecting elements and long connecting elements can connect specific points on crowns of one ringlet to specific points on crowns of the adjacent ringlet. The short connecting elements restricts flexibility but bring higher bending stiffness to the tubular support structure of the medical device.

According to an example, the short connecting elements can connect peaks of two adjacent ringlets, i.e. one end of the short connecting element is connected to a peak formed a ringlet and other end is connected to a similar peak formed in the adjacent ringlet. In an example, the short connecting elements connect to ringlets in such a way that there is no offset between the connected peaks, i.e., the short connecting element can connect in-line peaks. Accordingly, the short connecting element is substantially parallel to the common longitudinal axis and can be at a right angle with the radial plane.

In another example, one or more long connecting element from among the plurality of long connecting elements and one or more short connecting element from among the plurality of long connecting elements are connected to a common crown. In said example, a single short connecting element and a single long connecting element can be connected at the same point where one side of the crown forms a valley for the long connecting element and the opposite side of the same crown forms a peak for the short connecting element on the opposite side.

During fabrication, flexural and strength related properties of the medical device can be customized by defining specific number of short connecting elements, if present in the design, in the tubular support structure and the long connecting elements present between ringlets. Accordingly, the tubular support structure can be easily crimped while having high flexibility. In the crimped state, the medical device can be mounted on a catheter and guided through the vessel or organ to the targeted vessel part for deployment. After reaching the deployment state, the tubular support structure is self-expanded or balloon-expanded to its final state.

Further, according to an example, two adjacent ringlets can be connected only by short connecting elements or long connecting elements. In other words, each ringlet is connected with adjacent ringlets through at least one connecting element, which can either be a short connecting element or a long connecting element. Further, the connecting elements can connect the ringlets alternatively or continuously, i.e., the long or short connecting element connect adjacent ringlets alternatively or they connect adjacent ringlets continuously.

In addition, the long connecting elements or the long connecting elements along with short connecting elements aid in minimizing the stress generation or stress concentration at potential locations due to different mechanical forces applied on the medical device at the time of deploying it or after its deployment. The mechanical forces may be, for example, elongation, compression, torsional movement, bending movement and other physiological conditions, for instance, blood flow (after the deployment). The presence of the long connecting elements or the long connecting elements along with short connecting elements restrict the stress generated or stress concentration or both in the stent due to the abovementioned factors. The properties of the stent, such as radial strength, fracture resistance, flexibility, bending strength, and stability, can be achieved by selecting combinations of long and short connecting elements in the medical device and by customizing the density of connecting elements between two ringlets and along the length of the medical device.

In addition, width of the straight struts forming the crowns, the long connecting elements, and the short connecting elements measured in the circumferential direction of the tubular support frame remain constant along a length of the particular element. Also, the thickness of the straight struts, the long connecting elements, and the short connecting elements measured in the radial direction of the tubular support frame also remains constant along the length.

The above aspects are further illustrated in the figures and described in the corresponding description below. It should be noted that the description and figures merely illustrate principles of the present subject matter. Therefore, various arrangements that encompass the principles of the present subject matter, although not explicitly described or shown herein, may be devised from the description and are included within its scope.

FIG. 1 illustrates a developed view of a medical device 100 showing a section of a tubular support structure 102 in an initial, crimped state according to an embodiment. In an example, the medical device 100 can be a stent. The medical device 100, according to the present subject matter, can be placed inside the lumen of human or animal, such as an artery, vein, bile duct, urinary tract, alimentary tract, tracheobronchial tree, cerebral aqueduct or genitourinary system. Specifically, the medical device 100 can be used in femoral artery, superficial femoral artery, popliteal artery, tibial artery, genicular artery, cerebral artery, carotid artery, vertebral artery, subclavian artery, radial artery, brachial artery, axillary artery, coronary artery, peripheral artery, iliac artery or neuro-arteries. For example, the medical device can be used to remedy stenosis in superficial femoral artery.

The tubular support structure 102, according to the present subject matter, can be formed of close cell, open cell or hybrid configuration. Further, the tubular support structure 102 is made of a material selected from metal, non-metal, alloy, polymer, biodegradable, bioresorbable material or a combination of two or more thereof. For example, all deformable, medically possible metal, metal alloy can be used and include but are not limited to Stainless steel, Cobalt alloys, pure Iron, Nickel-titanium alloys, Tantalum, Niobium, Nickel alloys, Magnesium alloys, Zinc alloys, L605, MP25N, and Nitinol. For instance, the material used for the medical device 100 deployable through balloon-expansion mechanism is selected from Cobalt Chromium, Stainless Steel, Magnesium, Platinum, bioresorbable polymer or a combination of two or more thereof. On the other hand, in said example, the material used for the medical device 100 capable of self-expanding operation is mainly a shape-memory alloy e.g. Nitinol.

In addition, examples of polymers that can be used to fabricate the medical device 100 in accordance with the present subject matter include but are not limited to polymers of L-lactide, Glycolide or combinations of thereof, poly(hydroxybutyrate), polyorthoesters, poly anhydrides, poly(glycolic acid), poly(glycolide), poly(L-lactic acid), poly(L-lactide), poly(D-lactic acid), poly(D-lactide), poly (caprolactone), poly(trimethylene carbonate), polyester amide, polyesters, polyolefins, polycarbonates, polyoxymethylenes, polyimides, polyethers, and copolymers and combinations thereof.

Further, the tubular support structure 102 can carry a biocompatible material, which in one case, can be a layer of the biocompatible material coated on the tubular support structure 102 using any coating technique. The biocompatible material can be a drug-eluting biocompatible material.

Figure 2:
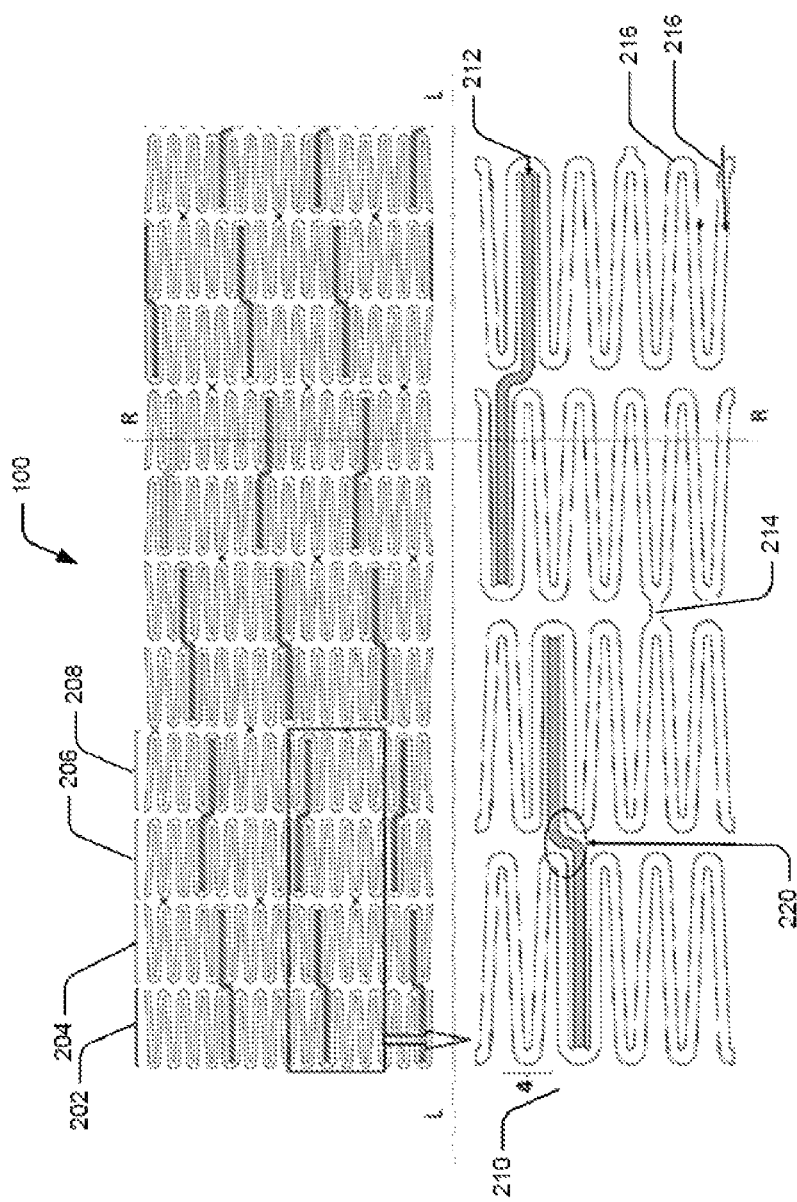
FIG. 2 illustrates a magnified view of a tubular support structure of the medical device, according to an embodiment of the present subject matter.
Figure 3A:
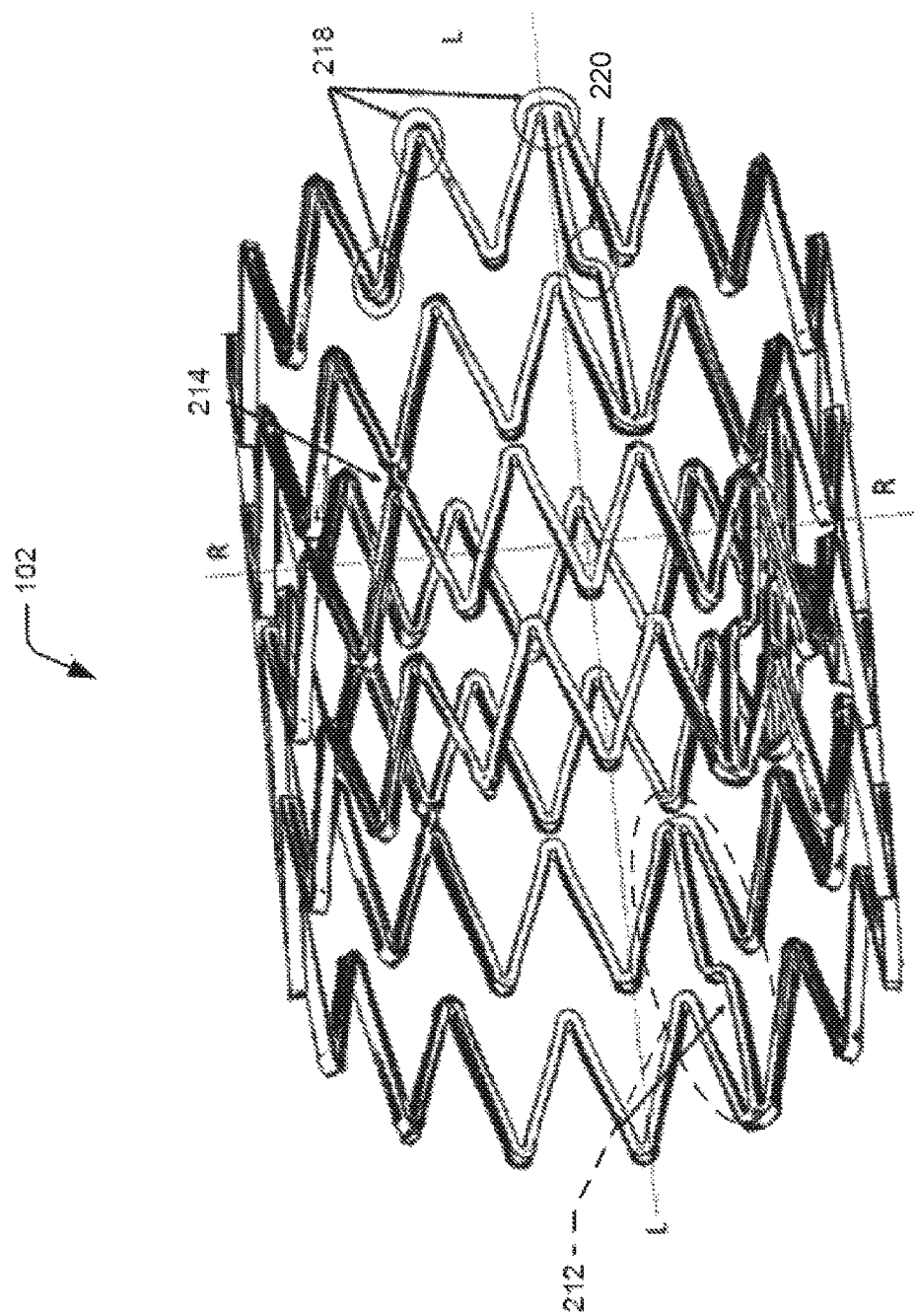
FIGS. 3A and 3B illustrates a magnified perspective view of the medical device in an expanded state, according to an embodiment of the present subject matter.
Figure 3B:
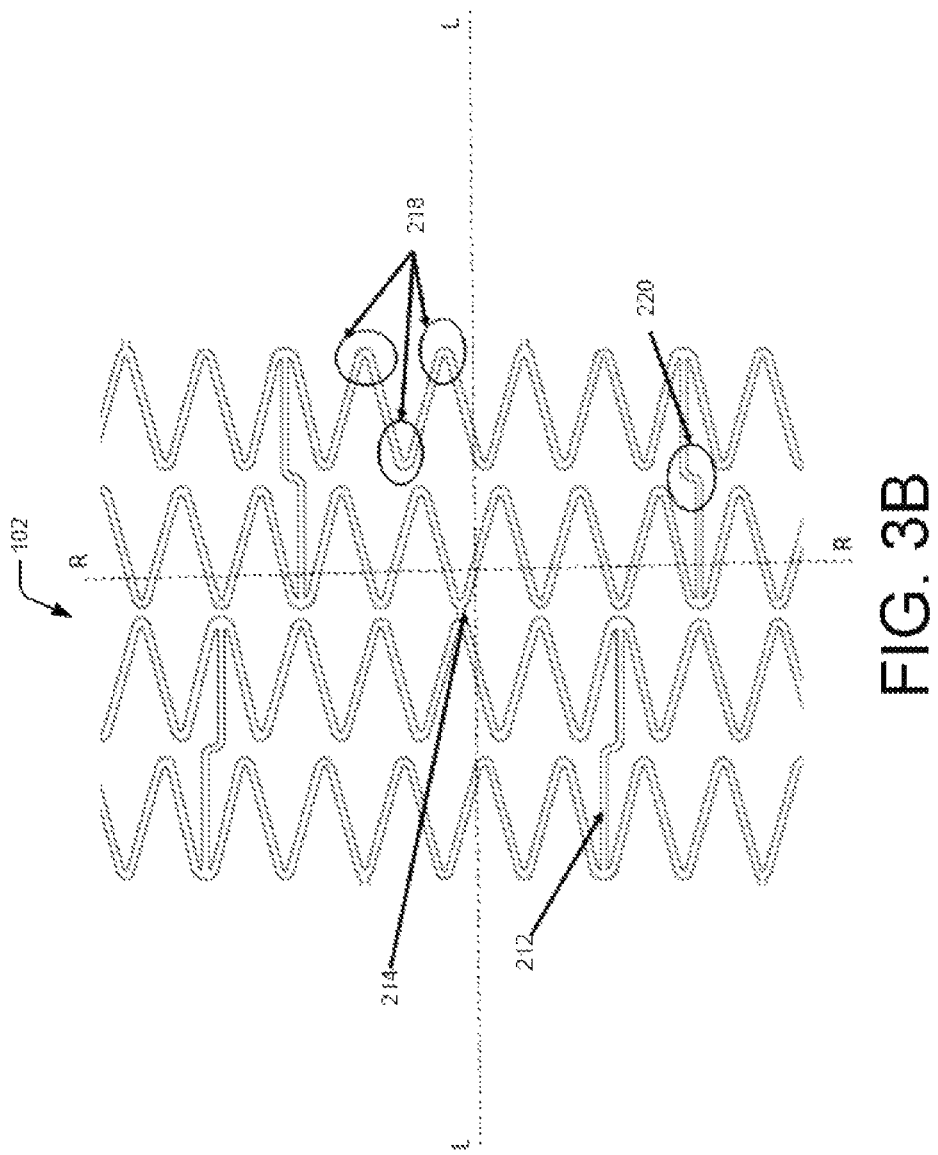

Structure of the tubular support structure 102 will now be described with respect to FIGS. 2, 3A, and 3B. FIG. 2 shows a magnified view of the medical device 100 showing a section of the tubular support structure 102 shown in FIG. 1. Further, FIG. 3a illustrates a perspective view of the tubular support structure 102 and FIG. 3b illustrates front view of the tubular support structure 102. According to an example, the tubular support structure 102 may be tubular in shape and is made of multiple ringlets for example 202, 204, 206 and 208. The ringlets for example, 202, 204, 206 and 208, are made of endless sequence of multiple crowns 210. In an example, each ringlet is formed of four to fifteen crowns 210. The tubular support structure 102 can be of different lengths and diameters. The length of the tubular support structure 102 depends on the number of ringlets 202 and the diameter of the tubular support structure 102 depend on the number of crowns 210 in each ringlet 202. Depending on the treatment required for a particular vessel or organ; the number of ringlets and number of crowns in each ringlet can be customized to prepare a suitable support structure for a specific vessel or organ treatment. In one example, the ringlets 202 are arranged sequentially in longitudinal axis direction and adjacent ringlets for example 204, 206 and 208 are connected through long connecting elements 212 or short connecting elements 214 in continuous manner. The crowns 210 are formed of struts 216 where struts are arranged in a V-shaped configuration 218 as shown in FIG. 3A. The width of the struts 216, long connecting elements 212, short connecting elements 214 measured in the circumferential direction of the tubular support structure 102 remain constant along their lengths. Also, the thickness of the struts 216, long connecting elements 212 and short connecting elements 214 measured in the radial direction of the tubular support structure 102 remains constant.

Short connecting elements 214 and long connecting elements 212 connect crowns of one ringlet to crowns of another adjacent ringlet in a predefined manner. In one example, short connecting elements 214 connect two adjacent ringlets in a peak-to-peak configuration whereas long connecting elements 212 connect two adjacent ringlets in a valley-to-valley configuration. Additionally, no two adjacent ringlets can have both type of connecting elements. Two adjacent ringlets for example 204, 206 can be connected only by short connecting elements 214 or long connecting elements 212. Additionally, the ringlets will be mandatorily connected with adjacent ringlets through at least one connecting element where the connecting element can be a short connecting element 214 or a long connecting element 212.

Figure 4:
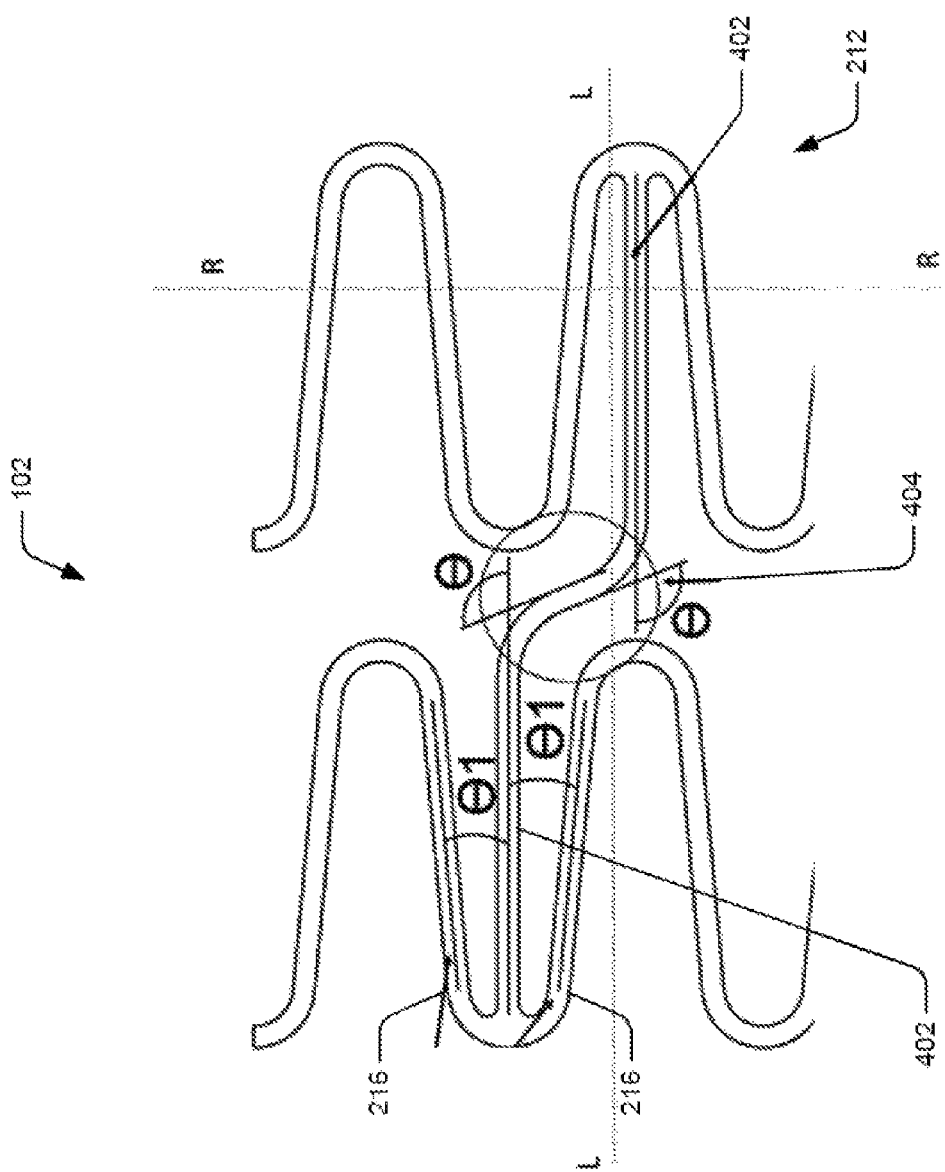
FIG. 4 illustrates a magnified view of connections formed in the tubular support structure, according to an embodiment of the present subject matter.

In one implementation, if two adjacent ringlets 202, 204 are connected through the long connecting elements 212 then the next two adjacent ringlets 204, 206 are connected using the short connecting elements 214. This design involving alternatively using both type of connecting elements between the ringlets 204 is followed across the length (longitudinal axis) of the tubular support structure 102 except the ends of the tubular support structure 102. If required, at the ends of the tubular support structure 102, the last one to three ringlets 202 from the end are connected using the short connecting elements 214 in peak-to-peak configuration. This is also shown in FIG. 4. The peak-to-peak connecting configuration between these ringlets 204 can be at all the peaks or at alternative peaks. However, it is possible to use either the long connecting elements 212 or short connecting elements 214 in continuous manner or in blocks. In continuous manner, all the ringlets 202, 204, 206, and 208 will be connected through either the long connecting elements 212 or short connecting elements 214. In blocks manner, some ringlets will be connected through one type of connecting elements and followed by this block, some others will be connected through another type of connecting element.

According to an aspect, as depicted in FIG. 1, FIG. 2, FIG. 3A, FIG. 3B, and FIG. 4, the long connecting elements 212 is of a Z-shaped configuration 220 and connects the ringlets 202, 204, 206, and 208 in valley-to-valley configuration i.e. one end of the long connecting elements 212 is connected to a valley-type formation formed between two struts 216 connected in a V-shaped configuration 218 in the crown 4 of a ringlet 202 and the other end of the long connecting elements 212 is connected to a similar valley formation in an adjacent ringlet 204. The long connecting elements 212 is formed of two long sections 402 and a short section 404. The short section 404 connects the ends of the two long sections 402 in such a way to form an obtuse angle θ between the short section 404 and the long section 402.

As a design element, angle θ is decided at the time of fabrication and remains fixed while crimping or expanding the tubular support structure. This angle θ can be designed between 91° and 160°, including both the angles. Due to this shape of the long connecting elements 212 and unchanging nature of this angle θ present in the long connecting elements 212; the length of the tubular support structure does not change axially after the tubular support structure is deployed in self-expansion mechanism. This feature of retaining original axial length of the tubular support structure, after the deployment of the tubular support structure, provides enhanced accuracy in treatment of the vessel or organ. In balloon expansion mechanism, the long connecting element 212 restricts or delays the change in axial length of the tubular support structure 102. Hence, in balloon-expansion mechanism, the length of the tubular support structure 102 contracts but minimally.

Similarly, the struts 216 also form an angle θ with the long section 402 of the long connecting elements 212. This angle θ is not fixed and increases or decreases depending on crimping or expansion. Combination of long connecting elements 212 with unchanging angle θ and expandable/crimpable peak/valley brings a desired set of required properties in a tubular support structure. Long connecting element 212 provides structural stability, flexibility whereas V-shaped peak/valley provides expandability. A straight long connecting element 212 has poor stress distribution and can pose a risk to the vessel during deployment of the balloon catheter. Having an angle in the long connecting elements 212 provides improved safety while the tubular support structure 102 is being maneuvered through the vessel to the target site. In addition, the unchanging angle θ in the long connecting element helps in managing the stress generation or stress concentration due to different mechanical forces applied on the tubular support structure 102 at the time of deploying it or after its deployment. Most commonly, these mechanical forces are elongation, compression, torsional movement, bending movement and other physiological conditions e.g. blood flow (after the deployment)

Figure 5:
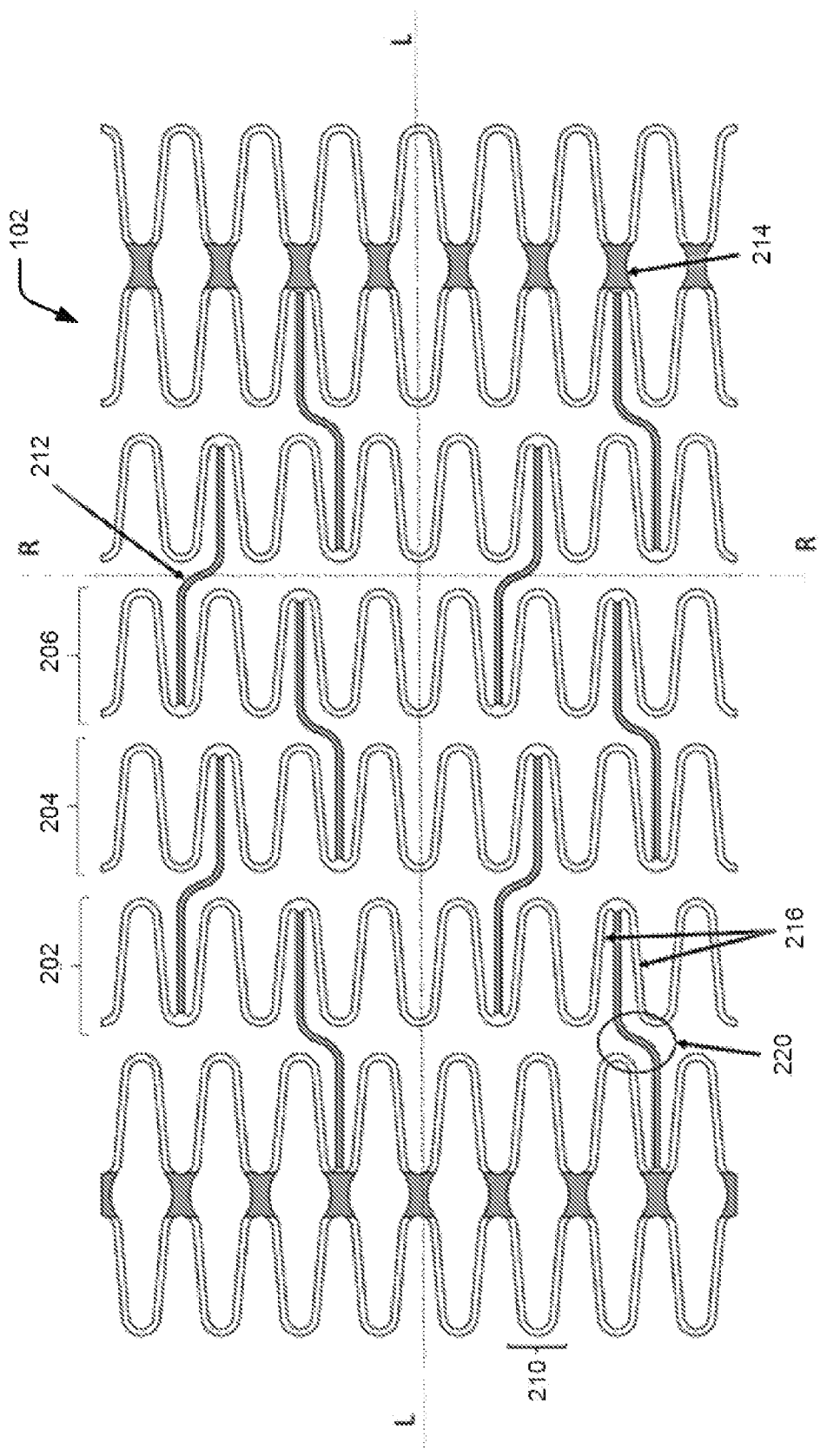
FIG. 5 illustrates the detailed view of a section of the medical device, according to another embodiment of the present subject matter.

FIG. 5 depicts another embodiment of the tubular support structure 102, according to the present subject matter, where the adjacent ringlets 202, 204 can be connected using only the long connecting elements 212 in a valley-to-valley configuration. Optionally, the last two ringlets 206 and 208 can be connected using the short connecting elements 214 in a peak-to-peak configuration. The peak-to-peak connecting configuration between these ringlets can be at all the peaks or at alternative peaks.

As seen in FIGS. 2, 4 and 5, as one moves along the tubular support structure in longitudinal direction; placement of the long connecting elements 212 is in such a way so that the long connecting elements 212 between two ringlets 202, 204 is mirror reflection of the long connecting element 212 present in next two ringlets 206, 208. This arrangement reduces strain development in one direction and bring greater stability, safety, radial stiffness, flexibility, fracture resistance and trackability. If all long connecting elements 212 are in one direction, it will bring an inherent tendency in the tubular support structure to deflect to one side which is not a required property and also poses risk to the patient.

As shown is FIGS. 1, 2, 3A, 3B, 4, 5 and 6, the short connecting elements 214 connect two adjacent ringlets in peak-to-peak manner i.e. one end of the short connecting element 214 is connected to a peak formed at adjoining point of two struts 216 in the ringlet 202 and the other end is connected to a similar peak formed in the adjacent ringlet 204. These two peaks are in same line longitudinally i.e. there is no offset. Hence, the short connecting elements 214 are at right angle to the radial axis and parallel to the longitudinal axis. In another embodiment, the short connecting elements 214 and long connecting elements 212 can adjoin a common point where two struts 216 will form a valley for the long connecting element 212 and the same two struts will form a peak for the short connecting element 214. The short connecting elements 214 provide low flexibility and high bending stiffness to the tubular support structure. During fabrication, flexural and strength related properties of a stent can be customized by defining specific number of short connecting elements 214 and long connecting elements 212 present in the stent between ringlets. Their specific combination will give specific set of properties. In specific cases, short connecting elements 214 are not included in the tubular support structure and the desired set of properties are obtained from presence of long connecting elements 212 only in the tubular support structure.

Additionally, FIGS. 3A and 3B show expanded views of the tubular support structure, according to an example. While FIG. 3A illustrates a perspective view of the tubular support structure of the medical device 100, FIG. 3B illustrates a two-dimensional view of the tubular support structure of the medical device 100. In FIGS. 3A and 3B, it can be seen that in expanded state, shape of long connecting element is unchanged. Also, there is no sign of buckling too whereas the crown formed due to V-shaped adjoining of struts 216 expands and increase the diameter of the tubular support structure.

Figure 6:
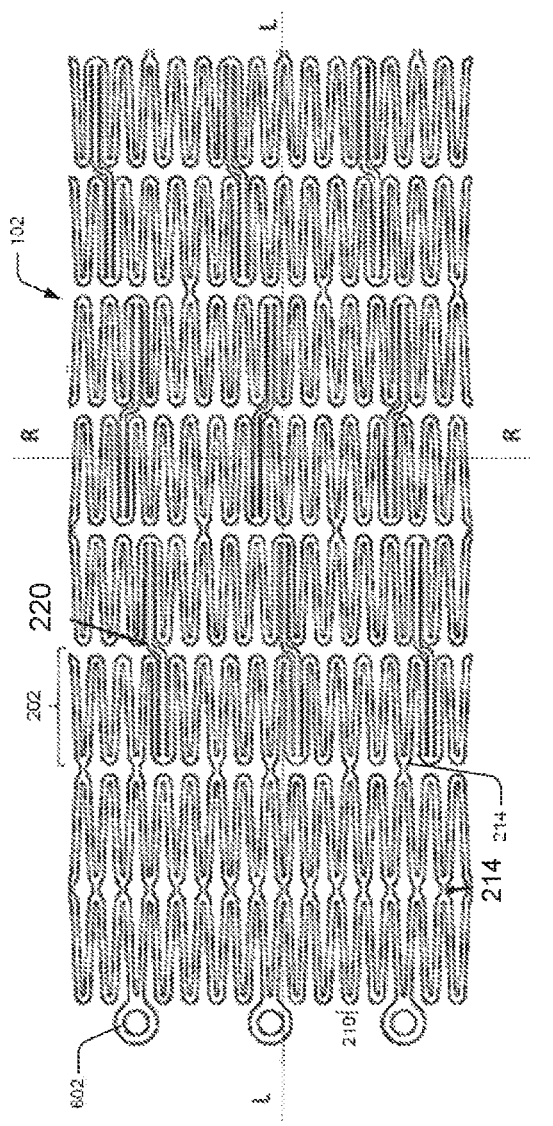
FIG. 6 illustrates anchor members of the tubular support structure of the medical device, according to an embodiment of the present subject matter.

FIG. 6 illustrates another embodiment of the medical device 100, where the tubular support structure 102 has at least one anchor member 602 attached to either one end or both the ends of the tubular support structure 102. The anchor member 602 prevents the tubular support structure 102 from moving axially or radially from the target site. In one case, the medical device 100 has multiple anchor members 602 at one end of the tubular support structure 102. In another case, the medical device 100 can have multiple anchor members at both the ends of the tubular support structure 102. The anchor members 602 at one or both ends of the tubular support structure 102 can have radiopaque markers to aid the physician in positioning the medical device under fluoroscopic imaging.

FIGS. 7A and 7B show an end-stopper 702 that is used with a tubular support structure 102, according to an example. While FIG. 7A illustrates a perspective view of the tubular support structure 102 with the end-stopper 702, FIG. 7B illustrates a two-dimensional view of the tubular support structure 102 with the end-stopper 702. The end-stopper 702 can be hollow, circular and can have a uniform diameter, for example, for uniform load distribution. In an example, the end-stopper 702 can be used with medical device 100 which are manufactured to be used as self-expanding stents. FIG. 7A shows the end-stopper 702 at the time of deployment, when a self-expandable support structure is being deployed in a vessel or organ. The end-stopper 702 is a hollow, circular structure of uniform diameter that is attached to an inner tube of a catheter and helps is uniform load transfer to the tubular support structure 102 at the time of deployment. The end-stopper 702 has peripheral slots or grooves 704 to accommodate anchor members 602 of the tubular support structure (also shown in FIG. 6). These slots or grooves 704 helps in better and uniform load transfer to the tubular support structure at the time of deploying the stent at the target site.

In addition, the present subject matter also envisages a method for fabricating the medical device 100 as explained above. For the manufacturing of the medical device 100, the method can involve, firstly, loading a medically clean and approved work-piece in a designing instrument. According to one example of the present subject matter, the work-piece or the specimen can be in shape of a hollow circular tube, a film, or a sheet. Then the required design of the medical device 100 is set-up or uploaded in the designing instrument, such as a computer-numerical controlled (CNC) machine for manufacturing. Subsequently, the required design is carved out of the work-piece to fabricate the medical device 100, such as a tubular support structure or a stent. In one example, the fabrication technique used in the designing instrument is selected from laser fabrication, chemical-etching, photo-chemical-etching or electro-discharge machining. For instance, the medical device 100 is fabricated by slitting a metallic hollow circular tube with a laser beam, the laser beam following a predefined cutting contour to produce the design of the medical device 100, as has been explained in the foregoing description of the present subject matter. Once the medical device 100 has been manufactured, the undesired material is removed from the surface of the medical device 100 for finishing. The cleaned and finished medical device 100 can then be polished or coated with an appropriate coating. For example, it can be coated with an anti-reactive agent which prevents it from reacting with the atmosphere where either the medical device 100 is stored or deployed. Additionally or alternatively, the medical device 100 can be covered with a medicinal substance, depending on the purpose, mode, and location of deployment of the medical device 100. Further, the tubular support structure 102 can be manufactured using 3D printing technique or additive manufacturing. 3D printing technique can be selected from Stereolithography (SLA), Digital light processing (DLP), Fused deposition modelling (FDM), Selective laser sintering (SLS), Selective laser melting (SLM), Electronic beam melting (EBM), Laminated object manufacturing (LOM), Polyjet technology or a combination of thereof.

Overall, the medical device 100 has high radial stiffness, zero or minimal axial length loss after deployment, enhanced flexibility and better bending stiffness. This ensures excellent and uniform bracing of the medical device 100 with the wall of the lumen, thereby providing effective support. The medical device 100, according to the present subject matter, can, therefore, be easily crimped and expanded through balloon-expandable delivery mechanism or self-expanded delivery mechanism. For example, the design supports easy crimping of the tubular support structure 102 during the deployment process. However, the inherent flexibility and stability due to the design helps in easy movement of the medical device 100 along the tortuous paths of a vessels during the implantation, with a higher safety level for both the patient and the physician.

Although design and application of the medical device 100 are described, it is to be understood that the present subject matter is not limited to the specific features or methods described. Rather, the specific features and methods are disclosed as implementations of the medical device 100.

We claim:

1. A medical device comprising:
a tubular support structure comprising:
a plurality of ringlets arranged sequentially along a common longitudinal axis thereof, wherein each of the plurality of ringlet is formed by of plurality of crowns connected along a circumferential direction, each crown being formed by two straight struts arranged in V-shaped configuration; and
a plurality of long connecting elements to connect the plurality of ringlets, wherein at least one of the plurality of long connecting elements connects adjacent ringlets, wherein consecutive long connecting elements connecting adjacent ringlets are to form a mirror-reflection of each other about a radial plane of reflection,
wherein at least one of the plurality of long connecting elements is formed of two long sections and a short section to form a Z-shaped configuration, wherein the long sections are parallel and the short section forms an obtuse angle with the long sections,
wherein the obtuse angle is unchanged while compressing or expanding the tubular support structure.

2. The medical device as claimed in claim 1, wherein each of the plurality of long connecting elements connects valleys of adjacent ringlets.

3. The medical device as claimed in claim 2, wherein each of the plurality of long connecting elements connects adjacent ringlets at an offset therebetween.

4. The medical device as claimed in claim 1, wherein the obtuse angle is between 91° and 160°.

5. The medical device as claimed in claim 1, further comprising a plurality of short connecting elements to connect the adjacent ringlets,
wherein each of the plurality of short connecting elements connects peaks of adjacent ringlets.

6. The medical device as claimed in claim 5, wherein the adjacent ringlets are connected through one of the plurality of short connecting elements or one of the plurality of long connecting elements.

7. The medical device as claimed in claim 6, wherein the plurality of ringlets is alternately connected by the plurality of short connecting elements and the plurality of long connecting elements.

8. The medical device as claimed in claim 5, wherein a long connecting element from among the plurality of long connecting elements and a short connecting element from among the plurality of short connecting elements are connected to a common crown.

9. The medical device as claimed in claim 5, wherein a width of each of the straight struts forming the crowns, each of the plurality of long connecting elements, and each of the short connecting elements measured in a circumferential direction of the tubular support structure is constant along a length thereof.

10. The medical device as claimed in claim 5, wherein a thickness of each of the straight struts, each of the long connecting elements, and each of the short connecting elements measured in a radial direction of the tubular support structure is constant along a length thereof.

11. The medical device as claimed in claim 5, wherein each of the plurality of short connecting elements that connect peaks of adjacent ringlets, connects in-line to the peaks in the adjacent ringlets.

12. The medical device as claimed in claim 1, comprising a coating of a biocompatible material.

13. The medical device as claimed in claim 12, wherein the biocompatible material is a drug-eluting biocompatible material.

14. The medical device as claimed in claim 1, wherein the tubular support structure is made of a biocompatible material made of at least one of a polymer, metal, alloy, non-metal, biodegradable, bioresorbable.

15. The medical device as claimed in claim 1, wherein the tubular support structure has a closed cell, open cell or hybrid configuration.

16. The medical device as claimed in claim 1, wherein the tubular support structure comprises at least one anchor member at least one end of the tubular support structure.

17. The medical device as claimed in claim 16, wherein the anchor member comprises a radiopaque marker.

18. The medical device as claimed in claim 1, further comprising an end-stopper comprising peripheral slots to accommodate anchor members of the tubular support structure.

19. The medical device as claimed in claim 1, wherein the tubular support structure is achieved from a hollow cylindrical tube using at least one of laser fabrication, chemical-etching, photochemical-etching, and electro-discharge machining.

20. The medical device as claimed in claim 1, wherein the medical device is fabricated using at least one of 3D-printing techniques and additive manufacturing.

21. The medical device as claimed in claim 1, wherein the medical device is used in treating abnormalities related to any one of an artery, tract, duct, and any conduit in animal or human body.

* * * * *